United States Patent
Edlauer et al.

(10) Patent No.: US 8,175,365 B2
(45) Date of Patent: May 8, 2012

(54) METHOD FOR REGISTERING A TWO-DIMENSIONAL IMAGE DATA SET, GENERATED USING FAN-SHAPED IMAGING RAYS, IN THE MEDICAL FIELD AND A CORRESPONDING COMPUTER PROGRAM PRODUCT AND METHOD AND SYSTEM FOR AUTOMATICALLY REGISTERING A BODY ON THE BASIS OF TWO-DIMENSIONAL IMAGE DATA, FOR USE IN MEDICAL NAVIGATION SYSTEMS

(75) Inventors: Martin Edlauer, München (DE); Uli Mezger, München (DE); Robert Essenreiter, München (DE); Manfred Weiser, München (DE)

(73) Assignee: Brainlab AG, Feldkirchen (DE)

( * ) Notice: Subject to any disclaimer, the term of this patent is extended or adjusted under 35 U.S.C. 154(b) by 371 days.

(21) Appl. No.: 12/427,789

(22) Filed: Apr. 22, 2009

(65) Prior Publication Data
US 2009/0268875 A1 Oct. 29, 2009

Related U.S. Application Data
(60) Provisional application No. 61/049,819, filed on May 2, 2008.

(30) Foreign Application Priority Data
Apr. 23, 2008 (EP) .................................. 08155032

(51) Int. Cl.
*G06K 9/00* (2006.01)
(52) U.S. Cl. ...................................................... 382/131
(58) Field of Classification Search .................. None
See application file for complete search history.

(56) References Cited

U.S. PATENT DOCUMENTS

| 5,610,964 | A  | * | 3/1997  | Flohr et al. ...................... 378/15 |
| 6,813,374 | B1 | * | 11/2004 | Karimi et al. ................. 382/131 |
| 2004/0127788 | A1 |  | 7/2004 | Arata |
| 2005/0152490 | A1 | * | 7/2005 | Shechter .......................... 378/4 |

FOREIGN PATENT DOCUMENTS

| DE | 103 34 163 | 3/2005 |
| EP | 1 192 913 | 4/2002 |
| WO | 2007/092841 | 8/2007 |

OTHER PUBLICATIONS

Office Action for corresponding Application No. EP 08 155 032.9 dated Nov. 27, 2008. Response to Office Action of Nov. 27, 2008 for corresponding Application No. EP 08 155 032.9 dated Mar. 3, 2009.
Office Action for corresponding Application No. EP 08 155 032.9 dated Jul. 30, 2009.
Response to Office Action of Jul. 30, 2009 for corresponding Application No. EP 08 155 032.9 dated Sep. 10, 2009.

* cited by examiner

*Primary Examiner* — Tu Nguyen
(74) *Attorney, Agent, or Firm* — Renner, Otto, Boisselle & Sklar, LLP

(57) ABSTRACT

The present invention relates to a method for registering a two-dimensional image data set, generated using fan-shaped imaging rays, in the medical field, wherein the method comprises: processing the two-dimensional image data on the basis of a spatial transformation function which describes a spatial relative position between points which have been imaged using a fan-shaped imaging ray, and the imaging apparatus used for imaging; and processing the two-dimensional image data on the basis of an imaging transformation function which describes an imaging function of the imaging apparatus used for generating the two-dimensional image data set, which describes a spatial relationship between the actual spatial position of imaged points and their imaging location in a recording.

12 Claims, 3 Drawing Sheets

Automatic Registration

METHOD FOR REGISTERING A TWO-DIMENSIONAL IMAGE DATA SET, GENERATED USING FAN-SHAPED IMAGING RAYS, IN THE MEDICAL FIELD AND A CORRESPONDING COMPUTER PROGRAM PRODUCT AND METHOD AND SYSTEM FOR AUTOMATICALLY REGISTERING A BODY ON THE BASIS OF TWO-DIMENSIONAL IMAGE DATA, FOR USE IN MEDICAL NAVIGATION SYSTEMS

RELATED APPLICATION DATA

This application claims the priority of U.S. provisional application No. 61/049,819, filed on May 2, 2008, which is hereby incorporated in its entirety by reference.

FIELD OF THE INVENTION

The invention relates to a method for registering a two-dimensional image data set, generated using fan-shaped imaging rays, in the medical field. The invention also relates to a method for automatically registering a body on the basis of two-dimensional image data which is suitable for use in medical navigation systems, in which the two-dimensional image data has been generated by means of fan-shaped imaging rays and are registered by means of the method in accordance with the invention. The invention also relates to a computer program product comprising a program code for performing the registering method in accordance with the invention. Lastly, the invention relates to a system for automatically registering a body on the basis of two-dimensional image data, for use in medical navigation systems. The body is for example the body of a patient or parts of the same, for example limbs or a torso.

BACKGROUND OF THE INVENTION

Many different methods for registering a body on the basis of different image data sets are already known in the prior art, wherein "registering a body" means that when said body is imaged, the exact spatial position of the body is ascertained. This enables spatial positions to be assigned to image data. In navigation-assisted operations, for example, this assignment enables surgical instruments to be moved precisely into positions which the surgeon has previously defined on the basis of recordings.

In the known registering methods, a distinction is drawn between manual methods and automatic registration methods. In the manual methods, for example, a pointer is used which indicates certain positions on a body which is to be imaged, wherein the position of the pointer is spatially determined. On the other hand, the position at which the pointer is situated is additionally specified manually in an available image data set. In this way, a body which is to be registered can be scanned using the pointer, and step by step, an assignment between spatial positions and image data points is obtained by point-mapping.

In automatic registering methods, a so-called calibrating phantom is for example used. While recording an image data set which is suitable for navigation purposes, a calibrating reference body is simultaneously also recorded, in addition to the body on which an operation is to be performed. The spatial position of this reference body is, however, known and is for example recorded by means of a camera system, wherein so-called marker devices are normally used which are identified by a camera system, wherein such a marker system is situated on the reference body, and another marker system which is simultaneously identified by the camera system is situated in a prior-known position relative to the recording apparatus—in most cases, on the recording apparatus itself. In this way, it is possible to automatically assign image data to spatial coordinates.

Although a number of different registering methods are already known, these registering methods are currently limited to certain types of image data sets. Image data sets on the basis of which registration can be performed currently include for example volumetric image data sets, i.e. three-dimensional data sets such as are for example generated by means of computer tomographs and magnetic resonance tomographs. Automatic registering methods for certain two-dimensional image data sets also exist, in which a conical recording ray is used. This is for example the case with recordings by means of C-arm-type x-ray apparatuses and with ultrasound recordings.

Fluoroscopic x-ray recordings in which the spatial position of the recorded body is known are also currently used to determine the spatial positions of points in three-dimensional CT recordings (so-called CT-fluoroscopic matching).

By contrast, a registration method which uses images generated using fan-shaped imaging rays is not known from the prior art, wherein a two-dimensional image data set is assembled from a number of fan-shaped imaging rays which are spatially offset relative to each other (for example shifted in parallel).

Fan-shaped imaging rays are characterized in that the imaging ray is broadly fanned in a certain preferred direction (the fanning direction), whereas in a direction orthogonal to the fanning direction, the imaging ray has extremely low flaring. The ratio approximately corresponds to 1 m (the detector-source distance) to 1 mm (the approximate thickness of a series of detectors in the Z direction).

A fan-shaped imaging ray is thus a specifically directed ray which is composed of a number of individual rays and lies substantially in one plane. The geometric properties of the fanned ray can thus be characterized in a good approximation by an angle in the plane, which describes the fanning of the fanned ray. Such fan-shaped imaging rays are for example generated prior to an actual CT recording using a computer tomograph. These so-called topograms or scout views are normally used to define the scanning region of the main recording. While in the actual CT recording, the radiation source is rotated around the body to be x-rayed and individual focused rays with no appreciable flaring are emitted, in two-dimensional CT-scan data, the radiation source is spatially fixed relative to the body, and a fan-shaped imaging ray is emitted. The body to be x-rayed is then passed under the radiation source and a number of fan-shaped recordings are taken, from which a two-dimensional image data set is then assembled. It is of course also possible to move the radiation source rather than the body. What is critical is the shifting of the body and the radiation source relative to each other.

It is the object of the present invention to provide an improved method for automatically registering a body on the basis of two-dimensional image data which is suitable for use by medical navigation systems, and a system for automatically registering a body on the basis of two-dimensional image data, for use in medical navigation systems.

SUMMARY OF THE INVENTION

The object is solved by a method for registering a two-dimensional image data set, generated using fan-shaped imaging rays, in the medical field, comprising the following steps: processing the two-dimensional image data on the basis of a spatial transformation function which describes a spatial relative position between points which have been imaged using a fan-shaped imaging ray, and the imaging apparatus used for imaging; and processing the two-dimensional image data on the basis of an imaging transformation function which describes an imaging function of the imaging apparatus used for generating the two-dimensional image data set, which describes a spatial relationship between the actual spatial position of imaged points and their imaging location in a recording; and by a system for automatically registering a body on the basis of two-dimensional image data, for use in medical navigation systems, comprising: an imaging apparatus, comprising: a generating unit for generating a fan-shaped imaging ray in order to image a body using the same; and a detection unit for detecting said fan-shaped imaging ray along its fanning direction, once it has passed through the body; and a computational unit, which is configured to: assemble a two-dimensional image data set from a number of spatially shifted images of a body; register the two-dimensional image data, on the basis of a spatial transformation function which describes a spatial relative position between imaged points which have been imaged using a fan-shaped imaging ray, and the imaging apparatus used for imaging, and on the basis of an imaging transformation function which describes an imaging function of the imaging apparatus used for generating the two-dimensional image data set, which describes a spatial relationship between the actual spatial position of imaged points and their imaging location in a recording, such that it is possible to navigate on the basis of the two-dimensional image data.

The sub-claims are directed to preferred embodiments of the invention.

A novel method for registering a two-dimensional image data set, generated using fan-shaped imaging rays, in the medical field forms the crux of the method in accordance with the invention and the system in accordance with the invention. It is in particular possible, on the basis of this method, to use the two-dimensional CT scan data described above for registration purposes and subsequent navigation purposes. This has the advantage that images with a high sharpness of detail can be used for registration and navigation, which enables more precise navigation.

Another advantage is that images can be used for navigation purposes which are produced prior to a CT recording anyway. This reduces the radiation exposure for a patient. The radiation exposure from two-dimensional CT scan recordings is also less than with a conventional fluoroscopic x-ray recording.

The method and system in accordance with the invention also have the advantage that no specific information concerning the imaging apparatus used and/or its transfer function is required. It is thus in particular possible to use the method in accordance with the invention irrespective of the manufacturer.

A method in accordance with the invention for registering a two-dimensional image data set, generated using fan-shaped imaging rays, in the medical field initially comprises a processing step which processes the two-dimensional image data on the basis of a spatial transformation function which describes a spatial relative position between points which have been imaged using a fan-shaped imaging ray, and the imaging apparatus used for imaging. A fan-shaped imaging ray is understood to mean an imaging ray which is emitted from a radiation source and experiences a significant flaring in a fanned shape in one dimension. The fanning of the ray is negligibly small in a direction orthogonal to said fanning direction. As a whole, all the fan-shaped imaging rays thus lie substantially in one and the same plane. A fan-shaped imaging ray can thus be detected by means of a detector which is linearly configured, for example in the form of a line detector. In this way, a two-dimensional image data set can be assembled from a number of fan-shaped imaging rays which are spatially shifted relative to each other, for example in parallel.

The spatial transformation function is preferably a function which only takes into account the spatial position of points and not, by contrast, certain imaging properties of an imaging apparatus. In a preferred example embodiment, the spatial transformation function describes a spatial relative position between points which have been imaged using a fan-shaped imaging ray, and the imaging apparatus used for imaging. The spatial transformation function allows a direct (i.e. one-stage) or indirect (i.e. multi-stage) transformation into a reference frame of the imaging apparatus. If reference is made to a number of points which are to be imaged or have already been imaged, then the position data of these points can be described in absolute values with respect to the coordinate system of the imaging apparatus. Alternatively, it is also possible to specify the position of imaged points relative to each other within said reference frame (that of the imaging apparatus). The type of coordinate system chosen can be chosen freely. It is for example possible to use Cartesian, cylindrical or spherical coordinates.

In a subsequent method step, the two-dimensional image data is processed on the basis of an imaging transformation function. This imaging transformation function describes an imaging function of the imaging apparatus used for generating the two-dimensional image data set, which in turn describes a spatial relationship between the actual spatial position of imaged points and their imaging location in a recording.

The imaging function when using a fan-shaped imaging ray differs substantially from the imaging function of a conical imaging ray such as is for example used when producing fluoroscopic images. The essential difference is that a fanned projection is used when imaging points by means of a fan-shaped imaging ray, whereas in the case of a conical imaging ray, a conical projection is used. When recording using a fan-shaped imaging ray, a fan-shaped plane—i.e. a two-dimensional area comprising X and Y coordinates—is approximately irradiated, and all the points imaged in this way are projected, wherein the projected points all lie approximately on a straight line. When recording using a conical imaging ray, by contrast, a three-dimensional spatial portion is x-rayed, and the points situated within this body are imaged onto a two-dimensional circular area. Thus, if the projections obtained (fanned ray projection and conical ray projection) are viewed, it is clear that the projection in the fanned projection is lower in dimensions than the projection in the conical projection. The imaging transformation function allows for this specific geometry which occurs in a fanned projection, and preferably, ascertaining the imaging transformation function is based on the approximation described. Other parameters which further characterize the fan-shaped imaging rays can advantageously include the planar fanning angle $\alpha$ (as opposed to a spatial angle which describes the aperture of a conical ray) and the distance between the radiation source and the detector and/or the linearly formed detection unit. This distance can for example be defined as the minimum path distance which an individual ray travels from the radiation source to the detection location.

In the method in accordance with the invention for registering a two-dimensional image data set, generated using fan-shaped imaging rays, the two-dimensional image data is processed on the basis of the described spatial transformation function and on the basis of the described imaging transformation function. This requires the spatial transformation function and the imaging transformation function to be known. They may be provided in the form of a data set, but can also be defined by inputting parameters (for example by inputting the fanning angle α used and the distance between the radiation source and the detector).

In accordance with a preferred embodiment of the method, it is possible for the imaging transformation function and the spatial transformation function to be ascertained first. This is necessary in particular when an imaging apparatus is used, the geometry of which has not been specified exactly. In this case, it is possible to take a reference measurement by means of a reference body which allows both the imaging transformation function and the spatial transformation function to be ascertained. To this end, the reference body is fitted with a number of points, the spatial position of which is known in relation to the imaging apparatus. On the other hand, when imaging using a fan-shaped imaging ray, these points can be assigned in the imaging plane and/or more specifically in the imaging straight line. Ascertaining the imaging transformation function and the spatial transformation function with the aid of such a reference body is described in detail further below with reference to FIG. 1.

In accordance with a preferred embodiment, geometric projections of points to be imaged, onto a fanning direction of the fanned ray (i.e. onto the imaging straight line), are taken into account for ascertaining the imaging function, wherein the points to be imaged are all situated in the plane which is covered and/or x-rayed by the fan-shaped imaging ray, wherein the points to be imaged are preferably at different heights above the detection straight line. Preferably, at least three different points for ascertaining the imaging function and their projections onto the imaging straight line are used, wherein the projection is performed such that for all the rays of the fan-shaped imaging ray, their respective ray path is considered, from which the imaging location of irradiated and/or x-rayed points on a body is acquired. The straight line onto which all the points are imaged defines the fanning direction of the fanned ray.

In accordance with a preferred embodiment, ascertaining the imaging function comprises ascertaining a proportionality factor which describes a relationship between spatial positions of points to be imaged, relative to each other, at a certain height above a detection plane of the imaging apparatus, and detection positions of the imaged points, relative to each other, in the fanning direction. Said detection plane is a narrow detection strip (imaging straight line). The longitudinal direction of said detection strip corresponds to the fanning direction of the fan-shaped imaging ray. As already described above, the fan-shaped imaging ray exhibits only negligible flaring in the direction orthogonal to said fanning direction. The detection plane can therefore consist of a linear arrangement of smallest detection units (for example, a line detector). Nonetheless, it is of course also possible to specify the height of a point above this plane on the basis of the planar properties, even when the detection plane is narrow. If, when imaging by means of a fan-shaped imaging ray, two points are situated in the irradiated plane, and if these points are situated at the same height above the detection plane of the imaging apparatus, and if these two points are arranged symmetrically with respect to the ray axis (the ray axis corresponds to a ray which, in a symmetrical overall arrangement, passes from the radiation source to the detection plane in the shortest possible distance), then it is immediately clear from the symmetrical relationships that the imaging locations of the points in the detection plane are also situated symmetrically with respect to the centre-point. In the case of this specific form of imaging, the presence of a proportionality factor follows directly from the intercept theorems of mathematics. The geometric relationships when imaging by means of a fan-shaped imaging ray are described in more detail further below with reference to FIG. 3.

The proportionality factor can be ascertained explicitly or implicitly. In the latter case, it is not explicitly output but rather implicitly provided by values of an imaging matrix.

The method in accordance with the invention for registering a two-dimensional image data set, generated using fan-shaped imaging rays, in the medical field can then be used in a method for automatically registering a body on the basis of two-dimensional image data which is suitable for use in medical navigation systems. To this end, the method steps of the registering method are combined for example with the following sequence of method steps in accordance with an embodiment: firstly, a fan-shaped imaging ray is generated by an imaging apparatus. The fan-shaped imaging ray has the same properties as have been generally described above. In particular, the fan-shaped imaging ray proceeds from an idealized punctiform radiation source and is significantly flared, substantially in one direction—the fanning direction—only. In a following step, a body is imaged by the fan-shaped imaging ray, wherein once it has passed through the body, the fan-shaped imaging ray is detected along its fanning direction. Said body can be an object or a patient or certain parts of a patient's body. A two-dimensional image data set is then assembled from a number of recordings of the body by means of the fan-shaped imaging ray, which are spatially shifted relative to each other. To this end, it is possible on the one hand to move the radiation source over the body, such that a number of different recordings are created. Alternatively, it is also possible for the radiation source to remain spatially fixed and the body or object to be passed incrementally under the radiation source, wherein a recording is taken by means of the fan-shaped imaging ray in each resting position of the body. What is critical is the relative movement between the imaging apparatus and the body. The shifted one-dimensional recordings are preferably recordings which are shifted parallel to each other and are each offset with respect to each other by a defined amount in a shifting direction. They are preferably shifted in a direction orthogonal to the fanning direction of the fan-shaped imaging ray. The two-dimensional image data set acquired in this way by being assembled from one-dimensional data is then subjected to the method in accordance with the invention for registering a two-dimensional image data set, generated using fan-shaped imaging rays, as described above.

In accordance with a preferred embodiment of the method for automatically registering a body on the basis of two-dimensional image data, a reference body is imaged. This reference body is on the one hand used for ascertaining a spatial relative position between the reference body and the imaging apparatus for the purpose of determining the spatial transformation function. On the other hand, the reference body is used for ascertaining the imaging function of the imaging apparatus, which describes a spatial relationship between the actual spatial position of points to be imaged and their imaging location. In accordance with a preferred embodiment, a reference body in the form of a cuboid is used. It is, however, also possible to use a round reference body. The reference body comprises different reference points. Some of these reference points can be identified, i.e. imaged, when imaging by means of the fan-shaped imaging ray. If the reference body is cuboid in shape, the reference points are preferably situated on different sides of the cuboid or at corners of the cuboid and are preferably made of materials having a high Z value (materials having a high atomic number, such as for example tungsten). They can be clearly recognized and assigned in the image generated. On the other hand, the reference body is provided with additional reference points which enable the spatial position of the reference body to be determined, wherein these can be conventional marker devices which are attached to the reference body and which are either active markers, i.e. markers which emit radiation, or passive markers, i.e. markers which reflect radiation. The radiation is preferably infrared radiation or ultrasound. The marker device preferably has three individual markers which are situated in a fixed position relative to each other. The position of the position markers and of the imaging reference points is known, such that the spatial position of the imaging reference points can be deduced from the spatial position of the markers. The spatial position of the reference body is ascertained on the basis of the marker devices in a way which is known in its own right, for example by means of a camera system which, at the same time as the marker devices of the reference body, detects at least one additional marker device which is attached in a known position relative to the imaging apparatus, and the relative position of the marker systems allows the position of the marker devices on the reference body to be determined. This is discussed even more specifically further below with reference to FIG. 1. The reference points of the reference body, which are identifiably imaged when imaging using the fan-shaped imaging ray, preferably all lie in the same plane, preferably in the plane which is covered by the fan-shaped imaging ray. The positions of the imaging reference points relative to each other are known.

In accordance with a preferred embodiment, the marker devices and the imaging reference points are not identical to each other, although their position relative to each other is known. Alternatively, it is also possible for reference points to simultaneously also serve as marker devices and as imaging reference points; for example, materials which allow an identification as an imaging reference point when imaging using a fan-shaped imaging ray (for example tungsten, in the case of x-ray recordings) can be incorporated in the interior of a reflective marker.

In accordance with a preferred embodiment of the method for automatically registering a body, the imaging resolution of the imaging apparatus in a direction orthogonal to the fanning direction approximately corresponds to a shift in position which describes the deviation between the actual position of a point to be imaged in said orthogonal direction and the position of its projection in said orthogonal direction. As already stated above, the fan-shaped imaging ray is significantly flared in the fanning direction only, whereas it exhibits only a very low flaring which is in principle negligibly small in the direction orthogonal to this. If the imaging relationships in the direction orthogonal to the fanning direction are viewed exactly, it is clear that a point situated at a certain spatial position in the orthogonal direction is shifted slightly in the imaging process in the direction orthogonal to the fanning direction. In the preferred embodiment, however, this shift is so slight that a point is nonetheless always detected by the same smallest physical detection unit, irrespective of its exact position in the direction orthogonal to the fanning direction, i.e. the imaging resolution of the imaging apparatus in the direction orthogonal to the fanning direction corresponds, in terms of its order of magnitude, to the shift in the position of the point in the direction orthogonal to the fanning direction which occurs during imaging. In other words, the geometric ray quality of the fan-shaped imaging ray is good enough that deviations from the ideal fan-shaped ray form are below the detection accuracy of the imaging apparatus.

In accordance with a preferred embodiment, a camera system is used for ascertaining the spatial relative position between the reference body and the imaging apparatus, wherein this can be a camera system which for example operates in the infrared range or in the ultrasound range. The camera system identifies a first marker device in a known position relative to the imaging apparatus, at the same time as a second marker device (as already described above), on the reference body: The first and second marker devices each comprise an identical marker system, wherein the markers can be active or passive markers, i.e. the markers emit a certain type of radiation or reflect a certain type of radiation. The first marker device is preferably attached fixedly to the imaging apparatus itself. However, it is also possible for the first marker device to be situated at a certain distance from the imaging apparatus, wherein the relative position of the imaging apparatus and the first marker device is known. The second marker device can be attached to the reference body from without; preferably, the second marker device is integrated into the reference body. A position of the second marker device relative to specific imaging markers of the reference body, which are identified by the imaging apparatus during imaging, is also known. This means that the distance between the second marker device and the specific imaging markers of the reference body is constant, and the directional orientation between the second marker device and the specific imaging markers is also known and does not change. This enables the relative positions between the specific imaging markers and the imaging apparatus to be ascertained by coordinate transformations. In accordance with a preferred embodiment, the markers of the second marker device are not identical to the specific imaging markers of the reference body which are identified by the imaging apparatus during imaging. However, it is also possible for the markers of the second marker device to be at least partially identical to the specific imaging markers. This depends on the physical nature of the imaging method and/or the type of radiation used.

In accordance with a preferred embodiment, the fan-shaped imaging ray is detected using a line detector, in particular an individual line detector. Preferably, only an individual line detector is used, since this is more cost-effective. The ray quality is also sufficient for the use of an individual line detector in many imaging apparatuses.

In the method for automatically registering a body, a fan-shaped x-ray is preferably emitted from a CT scanner. Such fan-shaped x-rays are in particular emitted from a CT scanner when topograms or scout views are to be produced prior to the actual CT recording, in order to define a scanning region. The method in accordance with the invention then enables the two-dimensional CT image data acquired in this way to additionally be used for registration purposes and subsequent navigation purposes.

In accordance with another aspect, the invention relates to a computer program product comprising a program code for performing the method described above for registering a two-dimensional image data set, generated using fan-shaped imaging rays, in the medical field, wherein it is immaterial which programming language the program code is written in or what medium the program code is stored on.

In accordance with another aspect, the invention relates to a system for automatically registering a body on the basis of two-dimensional image data for use in medical navigation systems. Medical navigation systems are preferably used in the medical field during operations, and in particular allow the position of surgical instruments to be precisely identified and/or allow said surgical instruments to be precisely positioned, so as to achieve a better treatment result, wherein the physician performing the treatment can track the current position of a treatment apparatus relative to a treatment object, for example a patient's body or a bone, in real time on the basis of a visual representation, for example on a monitor. The image data on the basis of which the physician navigates is registered image data, i.e. the precise spatial position of image data in relation to a previously defined reference (for example, the patient's body) has been defined beforehand by the system.

The system for automatically registering a body on the basis of two-dimensional image data for use in medical navigation systems comprises an imaging apparatus and a computational unit.

The imaging apparatus comprises a generating unit for generating a fan-shaped imaging ray in order to image a body using the same, and also comprises a detection unit for detecting said fan-shaped imaging ray along its fanning direction, once it has passed through the body. The generating unit preferably comprises a punctiform radiation source. Said radiation source preferably generates a directed ray. Alternatively, it is also possible to generate a directed imaging ray using a corresponding aperture system. The fanned shape of the imaging ray is preferably formed using apertures. The detection unit can be any known detection unit. The fanning direction of the fan-shaped imaging ray is to be understood as already described above in the description of the method for registering a two-dimensional image data set, generated using fan-shaped imaging rays, in the medical field.

The computational unit of the automatic registration system in accordance with the invention is configured to assemble a two-dimensional image data set from a number of spatially shifted images of a body, wherein the body to be imaged is preferably set into a relative movement with regard to the imaging apparatus, i.e. the body is for example passed under the imaging apparatus, or the imaging apparatus is passed over the body, wherein a recording is generated using the fan-shaped imaging ray in certain positions which are preferably shifted relative to each other by a fixed amount. In principle, however, it is also possible to provide a number of generating units and a number of detection units sequentially, which each generate a fan-shaped imaging ray, in order to image a body using the same, wherein each fan-shaped imaging ray x-rays a different plane of the body. For reasons of efficiency, however, a relative movement between the body and the imaging apparatus is to be preferred. In each recording by means of the fan-shaped imaging ray, a one-dimensional line of the two-dimensional image data set is generated. The two-dimensional image data set is in turn assembled from a number of lines.

The computational unit is also configured to register the two-dimensional image data, on the basis of a spatial transformation function which describes a spatial relative position between the imaged points which have been imaged using a fan-shaped imaging ray, and the imaging apparatus used for imaging, and on the basis of an imaging transformation function which describes an imaging function of the imaging apparatus used for generating the two-dimensional image data set, which describes a spatial relationship between the actual spatial position of imaged points and their imaging location in a recording. With regard to the characteristics of the spatial transformation function and the imaging transformation function, reference is made to the passages above in which the imaging transformation function and the spatial transformation function have already been discussed in detail within the framework of the description of the registration method.

In accordance with a preferred embodiment, the system comprises a camera unit, a first marker device and a reference body. The camera unit can for example be an infrared-sensitive camera unit or an ultrasound detection device. The first marker device is identified by means of the camera unit; to this end, the marker device is provided with corresponding markers which can operate as active signal emitters or as reflectors, wherein the first marker device is situated in a known position relative to the imaging apparatus; preferably, the first marker device is fixedly connected to the imaging apparatus and defines a coordinate system of the imaging apparatus. The reference body which is imaged by the imaging apparatus has a second marker device which is identified by the camera unit at the same time as the first marker device. The reference body also comprises specific imaging markers which can be identified when imaging using the imaging apparatus, wherein the second marker device and the specific imaging markers are situated in a known position relative to each other. Preferably, there are at least three specific imaging markers. At least three specific imaging markers are situated in one plane, namely the plane which is x-rayed by the fan-shaped imaging ray. Using the camera unit described, the first marker device and the reference body comprising its second marker device and the specific imaging markers, the computational unit is capable of: ascertaining the relative position between the first and second marker device; ascertaining, on the basis of this, the relative position between the specific imaging markers and the first marker device; ascertaining, on the basis of a recording of the reference body comprising its specific imaging markers, the imaging function of the imaging apparatus which describes a spatial relationship between the actual spatial position of points to be imaged and their imaging location in the recording using the fan-shaped imaging ray; and linking together the information acquired in this way for registering the two-dimensional image data set. It is then possible, on the basis of the registered two-dimensional image data set, to use a treatment apparatus such as for example a scalpel, navigationally assisted, in an operation. To this end, the treatment apparatus is provided, at a known position, with a marker device which is also identified—at the same time as the first marker device—by the camera system. Using a computational unit, the position of the treatment apparatus is determined from the camera data and visually displayed (in the registered image data set).

In accordance with a preferred embodiment, the reference body comprises at least three specific imaging markers which are all arranged in the plane of the fan-shaped imaging ray during an imaging process and are thus all imaged. The plane spanned by the three specific imaging markers is preferably identical to the main plane of the fan-shaped imaging ray. Small deviations between the planes can, however, be tolerated as long as these deviations are small enough that they cannot be resolved by the detection device used.

Preferably, the imaging apparatus emits a fan-shaped imaging ray which is flared in a direction orthogonal to the main fanning direction approximately to such an extent that the flaring approximately corresponds to the resolution of the detection unit in this direction. When using a line detector, in particular a one-line line detector, this means that the ray quality of the fan-shaped imaging ray, geometrically speaking, is very high. The flaring in the direction orthogonal to the fanning direction is negligibly small for practical purposes. Shifts in the position of points in the direction orthogonal to the main fanning direction are small enough that they cannot be detected by means of the detection device.

In accordance with a preferred embodiment, the imaging apparatus is a CT scanner which is configured to emit a fan-shaped x-ray in order to detect it using a line detector. This is often the case with conventional CT scanners when the latter generates a scout view or topogram which is used to define a scanning region for the actual three-dimensional CT recording.

BRIEF DESCRIPTION OF THE DRAWINGS

The present invention shall be understood even better by referring to the following figures.

DETAILED DESCRIPTION

Figure 1:
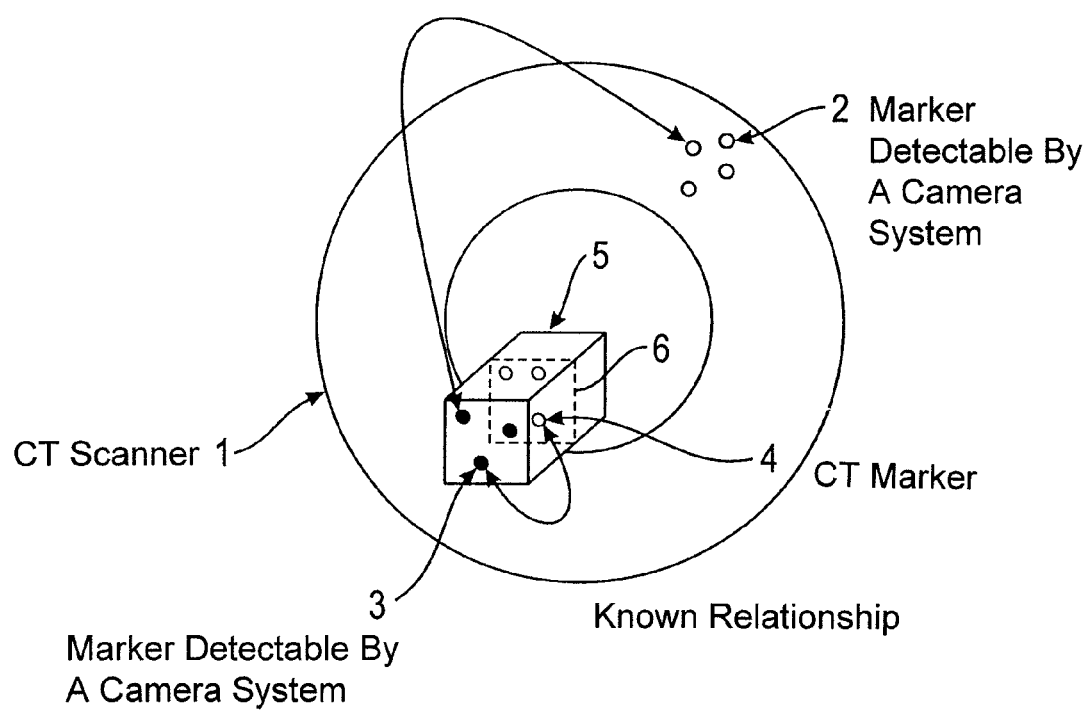
FIG. 1 shows a set-up for automatic registration using a cuboid reference body.

In the set-up for automatic registration using a reference body as shown in FIG. 1, the geometric relationships between the reference body 5 and the CT scanner 1 are shown in a partially perspective representation. The CT scanner 1 is shown in a linear top view onto the CT ring, whereas the reference body 5 is shown in the form of a cuboid which shows perspective. This serves to simplify the representation. The cuboid reference body 5 comprises two different marker systems: on the one hand, the reference body has three CT markers 4 which can be identified when imaging by means of the CT scanner (so-called specific imaging markers). These three CT markers 4 are situated in a plane 6 which is indicated by the dotted line of a section in the reference body 5. In a CT recording by means of a fan-shaped imaging ray, this plane 6 is detected by the fanned ray, such that all the CT markers 4 are imaged.

The reference body 5 also comprises three markers 3 of a marker device which are visible to a camera system. In the present example, they are passive markers which reflect radiation of a certain wavelength (in this case, infrared). The three markers 3 which can be identified by the camera system (not shown) are referred to in the following as position markers, in order to distinguish them from the specific imaging markers 4. The position markers 3 are attached on a facing area of the cuboid reference body and, in the example embodiment, define an area parallel to the area spanned by the imaging-specific markers 4. The relative distance between the position markers 3 and the imaging-specific markers 4 is known. In the example embodiment described, the distance between the facing area and the sectional area 6 is also in particular known. The position of the position markers 3 relative to each other is also known, as is the position of the imaging-specific markers 4 relative to each other. The position of at least one position marker 3 relative to at least one imaging-specific marker 4 is also known. Ultimately, enough parameters are available to allow the position of the imaging-specific markers 4 relative to the position markers 3 and the reference frame spanned by them to be described.

In the example embodiment described, markers 2 are attached to the CT scanner 1 which can also be identified by a camera system. In the example embodiment described, they are again passive markers, i.e. markers which reflect a certain type of radiation (in this case: infrared radiation). On the basis of the markers 2, it is possible to describe any points in a coordinate system of the CT scanner 1, wherein it is possible to specify absolute position data of points in said reference frame of the CT scanner 1. However, it is also possible to specify relative positions of points in this reference frame and to store them in the form of data.

The markers 2 which are attached to the CT scanner 1, and the position markers 3 which are attached to the reference body 5, are orientated such that they can be simultaneously identified by a single camera system (not shown). If the position of the markers 2 on the CT scanner 1 is then known, and if the position of the position markers 3 on the reference body 5 is determined within the framework of the automatic registration method which is known in its own right, then with the aid of the position determined in this way, it is also possible to deduce the spatial position of the specific imaging markers 4 in the reference frame of the imaging apparatus (i.e. with respect to the markers 2 on the CT scanner 1). The function which links the position of the specific imaging markers 4 to the reference frame of the CT scanner 1 is the spatial transformation function already described.

Figure 2:
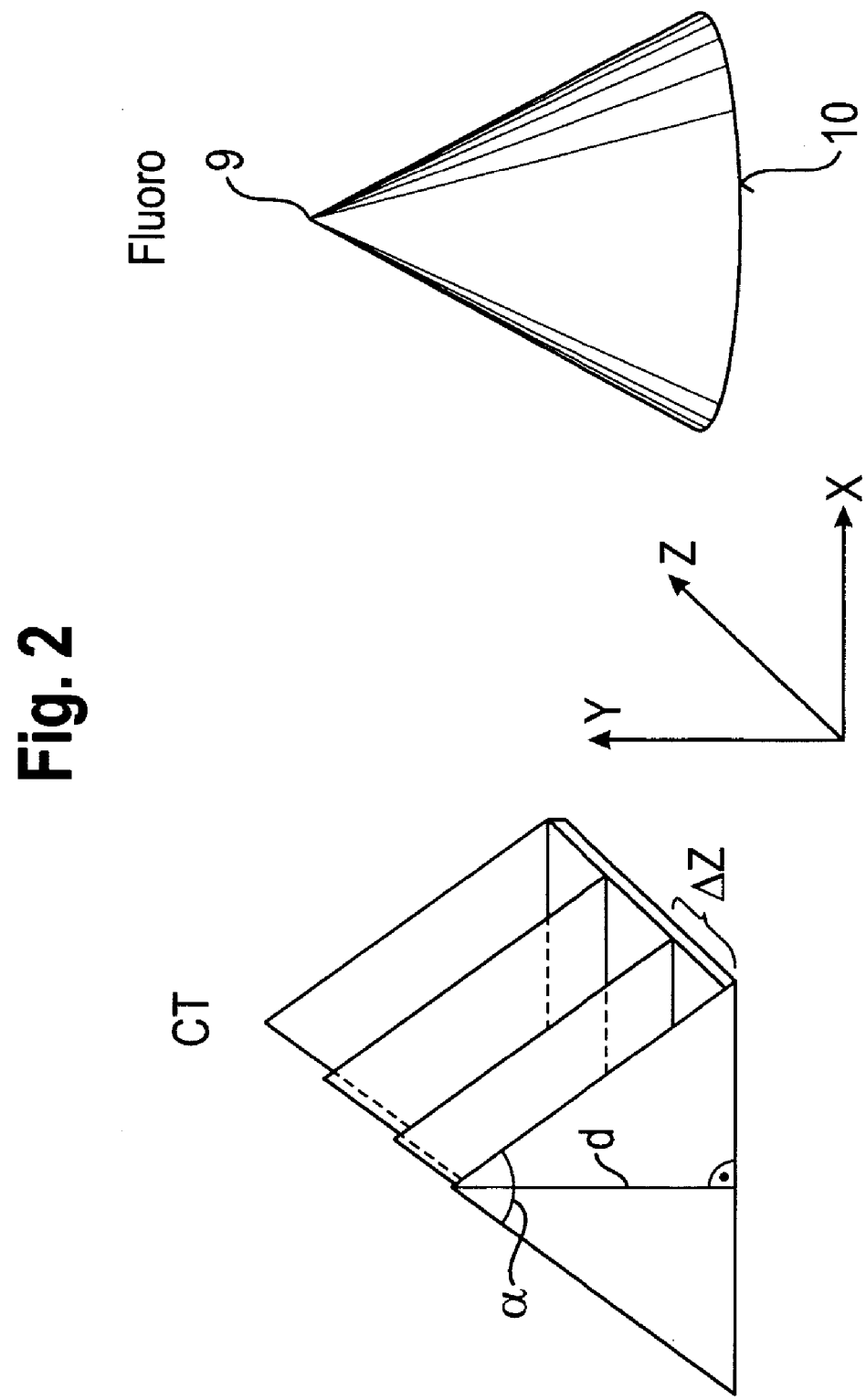
FIG. 2 shows a CT fanned ray projection in comparison with a conical ray projection when recording a fluoroscopic image.

FIG. 2 shows the geometric relationships in a fanned ray projection in comparison with a conical ray projection. In the present example, x-rays are used as the imaging rays and are shown in a comparison. The fan-shaped imaging rays such as are used in a CT pre-scan are shown on the left in FIG. 2; the so-called topograms or scout views (two-dimensional representations) are generated. The conical imaging ray of a conventional x-ray source, which generates a conventional fluoroscopic image, is shown in the right-hand half of the figure.

The fan-shaped imaging rays on the left in FIG. 2 are shown in an idealized form. They are also treated as idealized in the image registration method in accordance with the invention. The fan-shaped imaging ray exhibits fanning in the fanning direction X. The fan-shaped imaging ray is also detected in this direction X. However, the fan-shaped imaging ray exhibits almost no extension in the orthogonal direction Z, i.e. in the direction orthogonal to the fanning direction X. A two-dimensional image data set is assembled from a number of individual images in the X direction. The individual images are spatially shifted parallel to each other by the amount $\Delta Z$. Each of the fan-shaped imaging rays exhibits the same planar fanning angle $\alpha$. The distance between the starting point of the rays (for practical purposes, this corresponds to the radiation source) and the detection unit in the X direction is indicated by d.

The right-hand half of FIG. 2 shows the geometric relationships in a fluoroscopic recording. Proceeding from the radiation source 9, a conical ray is emitted. The aperture angle of the conical ray is a spatial angle. The main ray direction runs in the direction of the Y axis. A conical spatial portion is irradiated with the x-rays. The image is inherently two-dimensional in nature; all the points are imaged in or projected into a circular segment 10 in the XZ plane.

The comparison between the CT fanned ray geometry and the conical ray geometry of the fluoroscopic recording very clearly shows that the projection in the CT fanned ray recording is lower in dimensions. In the CT fanned ray recording, the projection is performed along a straight line (in the direction of the x axis); in the projection exhibiting a conical ray profile, the projection is performed into a two-dimensional plane, the XZ plane.

Figure 3:
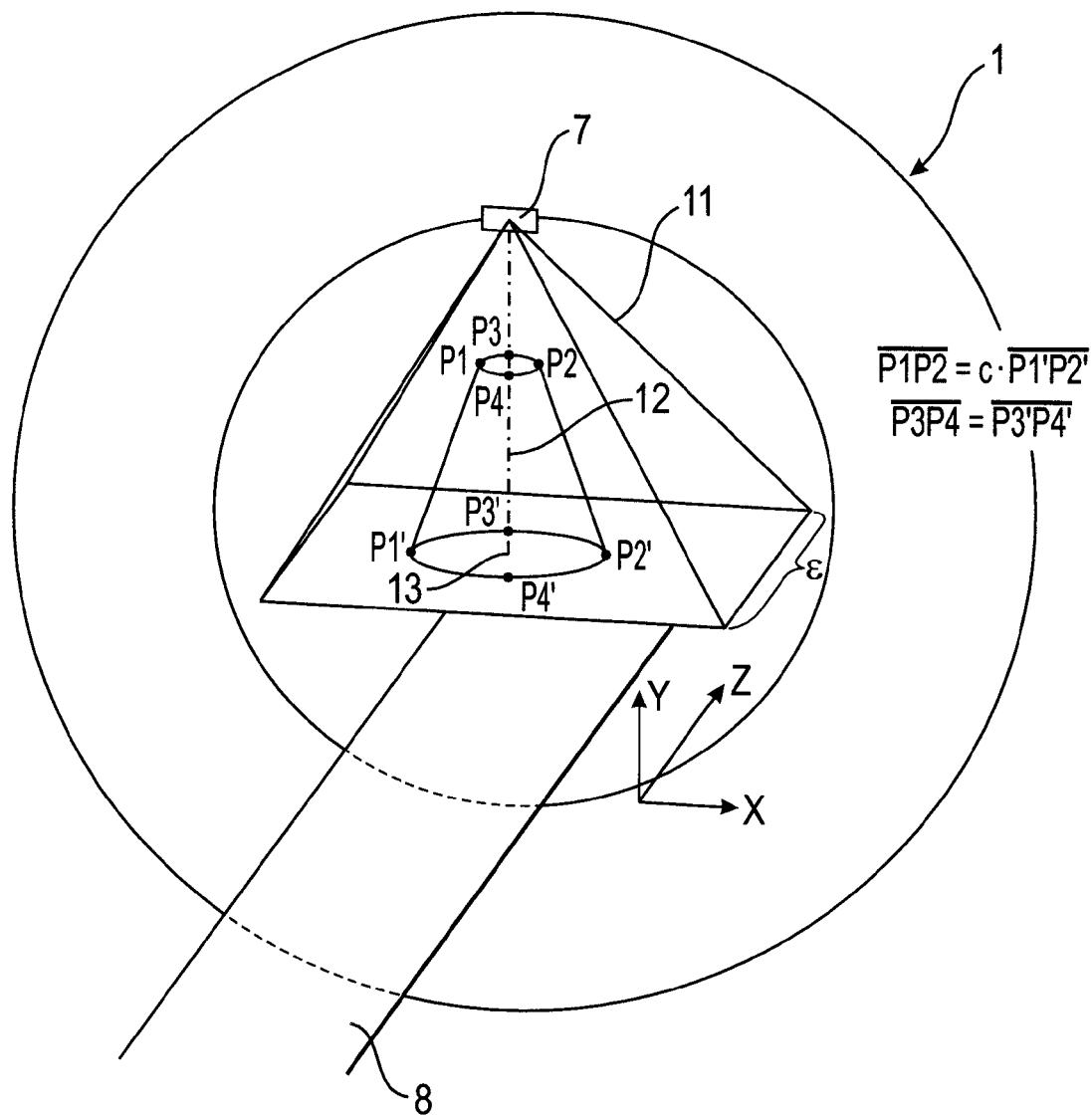
FIG. 3 shows the geometric relationships when imaging points by means of a fan-shaped x-ray.

FIG. 3 shows the geometric relationships when imaging and/or projecting individual points, when a fan-shaped imaging ray is used. The CT scanner 1 is again shown, to which an x-ray radiation source 7 is attached in a fixed position. Said x-ray radiation source 7 emits a fan-shaped x-ray 11, wherein the flaring of the ray in the direction orthogonal to the fanning direction X is shown in a significant exaggeration. The flaring of the ray in the Z direction is exceedingly small and is indicated here by $\epsilon$. The two-dimensional image data set, composed of a number of individual recordings using one fan-shaped imaging ray each which are shifted parallel to each other in the Z direction, includes entries in the X and Z directions. In the example embodiment, the XZ plane is the plane in which a CT table 8 is situated which can be moved relative to the x-ray radiation source 7.

A system of points P1, P2, P3 and P4 is then considered in FIG. 3. The points P1 and P2 are situated at a certain height above the detection plane (the XZ plane), i.e. they have the same Y coordinate. If the origin of the XYZ coordinate system is set at the imaging point 13, into which a ray is imaged along the main axis 12 of the fan-shaped imaging ray, then the points P1 and P2 have the same X coordinates in terms of magnitude. It may also be assumed that P1 and P2 exhibit the same Z coordinate. The points P1 and P2 are then imaged into the points P1' and P2', which in turn exhibit identical Y and Z coordinates (in the present case, Y=Z=0), and the X coordinates of P1' and P2' are identical in terms of magnitude. For imaging the points P1 and P2 onto P1' and P2', the following relationship applies: $\overline{P1P2}=c\cdot\overline{P1'P2'}$. The distance $\overline{P1P2}$ and the distance $\overline{P1'P2'}$ are linked together via the proportionality factor c. The same type of linking via the proportionality constant c applies to all the distances between points Pa and Pb which exhibit the same Y coordinate and X coordinates which are identical in terms of magnitude. If the points Pa and Pb to be imaged are situated at a different height above the detection plane (the XZ plane), i.e. they have a different Y coordinate than in the example just described, then the proportionality factor c changes. The proportionality factor c is thus a function of the height (the Y coordinate in FIG. 3) and/or the distance between the point to be imaged and the radiation source.

In accordance with a preferred embodiment, the proportionality factor c is not explicitly determined; instead, the law of imagery is ascertained. To this end, an imaging matrix is determined. Such an imaging matrix has a simpler form for the fanned ray image used than for example for fluoroscopic images. The imaging matrix for a fanned ray image is in particular lower in dimensions.

Since the geometric relationships in a projection onto the X direction have been described, the geometric relationships in the much more strongly focused and/or barely flared ray direction Z shall now be briefly discussed. The points P3 and P4, which exhibit the same X and Y coordinate and are to be imaged, are considered. The points P3 and P4 do, however, differ slightly in their Z coordinate. When imaging the points P3 and P4 onto the points P3' and P4' in the XZ plane, it may be seen that the X and Y positions of the points P3' and P4' are again identical, but that the Z coordinate differs slightly. This difference in the Z coordinate of the points P3' and P4' is, however, extremely small and is below the resolution of the detector which is used in the embodiment described by way of example. The maximum distance between imaged points P3' and P4' in the Z direction is $\epsilon$. However, the resolution of the line detector used is greater than or equal to $\epsilon$, i.e. when detected, the points P3' and P4' are in any case assigned to the same Z value. Thus, the following relationship approximately applies: distance $\overline{P3P4}=\overline{P3'P4'}$.

Although imaging the points P1, P2, P3 and P4 onto the points P1', P2', P3' and P4' has been described in FIG. 3, it is clear that also when projecting three points, as for example represented by the specific imaging markers 4 of the reference body 5, the geometric relationships are in principle the same.

It is thus possible to deduce the imaging transformation function from the geometric relationships when imaging the specific imaging markers 4 by means of a fan-shaped imaging ray 11.

In order to more simply describe the geometric ray relationships, the origin of the coordinate system XYZ was set on the detection plane XZ. Alternatively, it is possible for the position of the x-ray radiation source 7 to be chosen as the coordinate origin. It is easily possible to convert the positions of the points to be imaged and the locations of their projection from one coordinate system into another coordinate system.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments.

Although the invention has been shown and described with respect to one or more particular preferred embodiments, it is clear that equivalent amendments or modifications will occur to the person skilled in the art when reading and interpreting the text and enclosed drawings of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment or embodiments illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A method for registering a two-dimensional image data set, generated using fan-shaped imaging rays, in the medical field, comprising:

processing the two-dimensional image data set on the basis of a spatial transformation function which describes a spatial relative position between points which have been imaged using the fan-shaped imaging ray, and an imaging apparatus used for imaging, wherein processing the two-dimensional image data set includes ascertaining the spatial transformation function; and processing the two-dimensional image data set on the basis of an imaging transformation function which describes an imaging function of the imaging apparatus used for generating the two-dimensional image data set, which describes a spatial relationship between the actual spatial position of imaged points and an imaging location of the imaged points in a recording, wherein processing the two-dimensional image data set includes ascertaining the imaging transformation function, wherein geometric projections of points to be imaged, onto a fanning direction of the fanned ray, are taken into account for ascertaining the imaging function, and wherein ascertaining the imaging function comprises ascertaining a proportionality factor which describes a relationship between spatial positions of points to be imaged, relative to each other, at a certain height above a detection plane of the imaging apparatus, and detection positions of the imaged points, relative to each other, in a fanning direction of the fan-shaped imaging ray.

2. A method for automatically registering a body on the basis of two-dimensional image data which is suitable for use in medical navigation systems, comprising:

generating a fan-shaped imaging ray using an imaging apparatus;

imaging a body using the fan-shaped imaging ray, wherein once the fan-shaped imaging ray has passed through the body, the fan-shaped imaging ray is detected along a fanning direction of the fan-shaped imaging ray;

assembling a two-dimensional image data set from a number of recordings of the body using the fan-shaped imaging ray, the respective recordings of the body spatially shifted relative to each other; and performing the method steps of the method in accordance with claim 1, such that it is possible to navigate on the basis of the two-dimensional image data set.

3. The method in accordance with claim 2, wherein a reference body is imaged for ascertaining a spatial relative position between the reference body and the imaging apparatus for the purpose of determining the spatial transformation function and for ascertaining the imaging function of the imaging apparatus, which describes a spatial relationship between the actual spatial position of points to be imaged and their imaging location.

4. The method in accordance with claim 2, wherein the imaging resolution of the imaging apparatus in a direction orthogonal to the fanning direction corresponds to a shift in position which describes the deviation between the actual position of a point to be imaged in said orthogonal direction and the position of its projection in said orthogonal direction.

5. The method in accordance with claim 2, wherein the fan-shaped imaging ray is detected using a line detector.

6. The method in accordance with claim 5, wherein the line detector is an individual line detector.

7. The method in accordance with claim 2, wherein a fan-shaped x-ray is emitted from a CT scanner.

8. A computer program embodied on a non-transitory computer readable medium, wherein when the computer program is executed by a processor, the steps according to claim 1 are performed.

9. A method for automatically registering a body on the basis of two-dimensional image data which is suitable for use in medical navigation systems, comprising:

generating a fan-shaped imaging ray using an imaging apparatus;

using the fan-shaped imaging ray to image a body, wherein once the fan-shaped imaging ray has passed through the body the fan-shaped imaging ray is detected along its fanning direction;

assembling a two-dimensional image data set from a number of recordings of the body using the fan-shaped imaging ray, the respective of recordings of the body spatially shifted relative to each other;

processing the two-dimensional image data set on the basis of a spatial transformation function which describes a spatial relative position between points which have been imaged using a fan-shaped imaging ray, and the imaging apparatus used for imaging;

processing the two-dimensional image data set on the basis of an imaging transformation function which describes an imaging function of the imaging apparatus used for generating the two-dimensional image data set, which describes a spatial relationship between the actual spatial position of imaged points and an imaging location of the imaged points in a recording such that it is possible to navigate on the basis of the two-dimensional image data set, wherein a reference body is imaged for ascertaining a spatial relative position between the reference body and the imaging apparatus for the purpose of determining the spatial transformation function and for ascertaining the imaging function of the imaging apparatus, which describes a spatial relationship between the actual spatial position of points to be imaged and their imaging location, wherein:

a camera system is used for ascertaining the spatial relative position between the reference body and the imaging apparatus;

the camera system identifies a first marker device in a known position relative to the imaging apparatus and a second marker device on the reference body; and a position of the second marker device relative to specific imaging markers of the reference body, which are identified by the imaging apparatus during imaging, is known; and the relative positions between the specific imaging markers and the imaging apparatus are ascertained by coordinate transformations.

10. A system for automatically registering a body on the basis of two-dimensional image data, for use in medical navigation systems, comprising:

an imaging apparatus, comprising:
a generating unit for generating a fan-shaped imaging ray in order to image a body using the fan-shaped imaging ray; and
a detection unit for detecting said fan-shaped imaging ray along a fanning direction of the fan-shaped imaging ray, once the fan-shaped imaging ray has passed through the body;

a computational unit, which is configured to:
assemble a two-dimensional image data set from a number of spatially shifted images of a body;
register the two-dimensional image data,
on the basis of a spatial transformation function which describes a spatial relative position between imaged points which have been imaged using a fan-shaped imaging ray, and the imaging apparatus used for imaging, and
on the basis of an imaging transformation function which describes an imaging function of the imaging apparatus used for generating the two-dimensional image data set, which describes a spatial relationship between the actual spatial position of imaged points and an imaging location of the imaged points in a recording, such that it is possible to navigate on the basis of the two-dimensional image data;

a camera unit;

a first marker device which is situated in a known position relative to the imaging apparatus and is identifiable by the camera unit;

a reference body which is imagable by the imaging apparatus and comprises:
- a second marker device which is identifiable by the camera unit; and
- specific imaging markers which are identifiable by the imaging apparatus during imaging, wherein the second marker device and the specific imaging markers are situated in a known position relative to each other;

wherein the computational unit configured to:
- ascertain the relative position between the first and second marker device;
- ascertain, on the basis of the ascertained relative position between the first and second marker device, the relative position between the specific imaging markers and the first marker device;
- ascertain, on the basis of a recording of the reference body comprising the specific imaging markers, the imaging function of the imaging apparatus which describes a spatial relationship between the actual spatial position of points to be imaged and their imaging location in the recording using the fan-shaped imaging ray; and
- link together the information acquired in this way for registering the two-dimensional image data set.

11. The system in accordance with claim 10, wherein the reference body comprises at least three imaging markers wherein during an imaging process the markers are all arranged in the plane of the fan-shaped imaging ray and are thus all imaged.

12. The system in accordance with claim 10, wherein the imaging apparatus emits a fan-shaped imaging ray which is flared in a direction orthogonal to the main fanning direction such that the flaring corresponds to the resolution of the detection unit in this direction, and/or wherein the imaging apparatus is a CT scanner which is configured to emit a fan-shaped x-ray and to detect the fan-shaped x-ray using a line detector.

* * * * *